United States Patent [19]
Bemis et al.

[11] Patent Number: 5,605,245
[45] Date of Patent: Feb. 25, 1997

[54] SHARPS DISPOSAL CONTAINER

[75] Inventors: Richard A. Bemis, Sheboygan; Kenneth V. Pepper, Plymouth, both of Wis.

[73] Assignee: Bemis Manufacturing Company, Sheboygan Falls, Wis.

[21] Appl. No.: 388,348

[22] Filed: Feb. 14, 1995

Related U.S. Application Data

[62] Division of Ser. No. 45,830, Apr. 9, 1993, Pat. No. 5,413, 243, which is a continuation of Ser. No. 651,294, Feb. 5, 1991, abandoned, which is a continuation of Ser. No. 309,208, Dec. 20, 1988, abandoned, which is a continuation-in-part of Ser. No. 40,430, Apr. 20, 1987, Pat. No. 4,736,860.

[51] Int. Cl.⁶ .................................................. B65D 43/00
[52] U.S. Cl. .......................... 220/324; 220/326; 220/908
[58] Field of Search ................................ 220/481, 908, 220/210, 224, 326, 324

[56] References Cited

U.S. PATENT DOCUMENTS

| | | | |
|---|---|---|---|
| 697,655 | 4/1902 | O'Leary. | |
| 2,754,991 | 7/1956 | Hagerty et al. | 220/18 |
| 4,453,648 | 6/1984 | Harris et al. | 220/908 X |
| 4,580,688 | 4/1986 | Harris et al. | 220/908 X |
| 4,715,498 | 12/1987 | Hanifl | 220/908 X |
| 4,779,728 | 10/1988 | Hanifl et al. | 220/908 X |
| 4,842,138 | 6/1989 | Sandel et al. | 220/908 X |
| 4,874,103 | 10/1989 | Quisenberry et al. | 220/908 X |
| 4,955,477 | 9/1990 | Bruno | 206/366 |
| 5,137,260 | 8/1992 | Pehr | 220/326 X |

*Primary Examiner*—Steven M. Pollard
*Attorney, Agent, or Firm*—Michael, Best & Friedrich

[57] ABSTRACT

A sharps container apparatus comprising a container including a door manually movable between a closed position and an open position, and a rubber band for biasing the door toward the closed position, the container being completely closed when the door is in the closed position, a bracket adapted to be securely mounted on a wall, and interengaging projections and slots on the bracket and on the container for securing the container to the bracket.

24 Claims, 5 Drawing Sheets

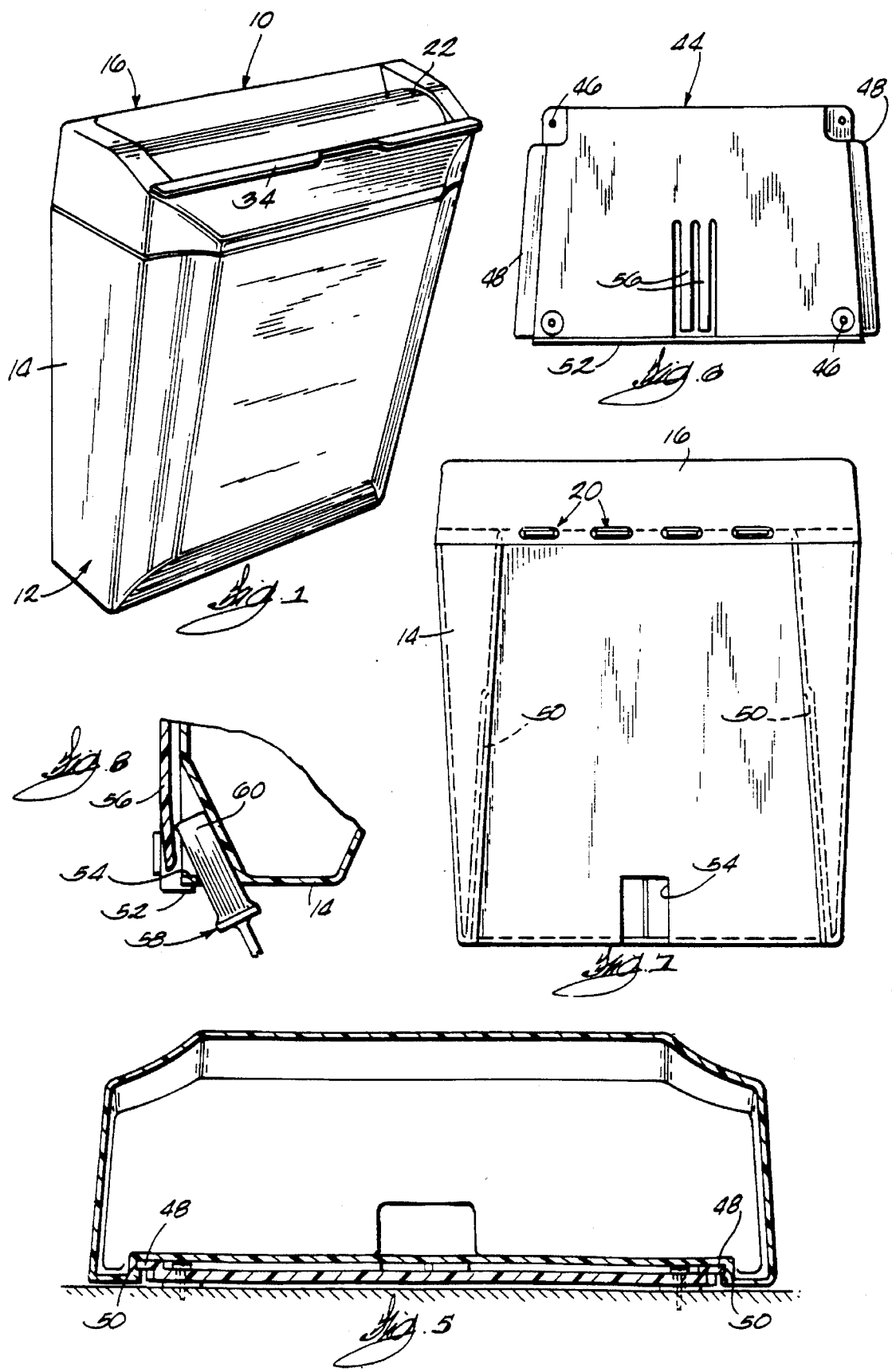

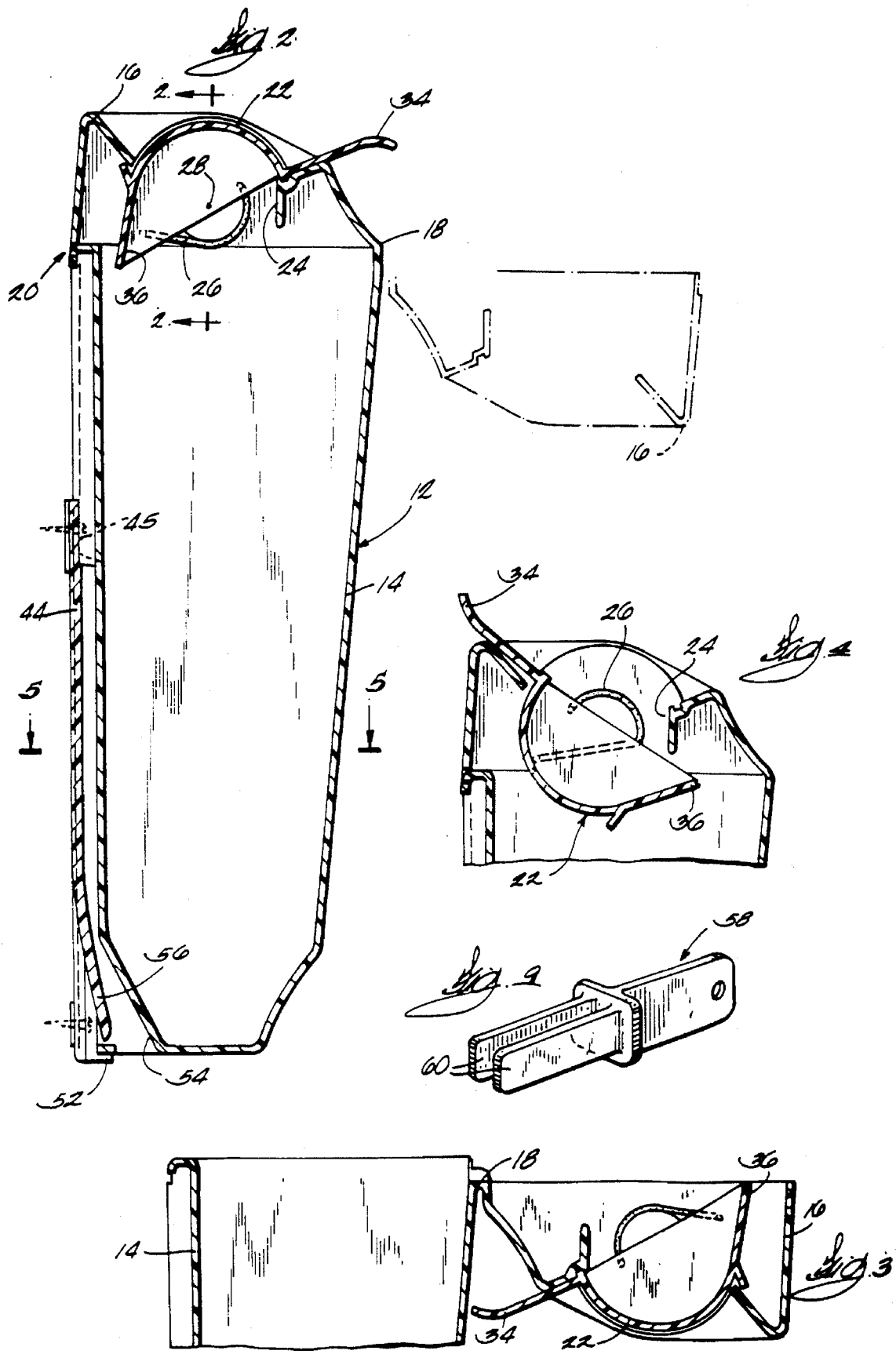

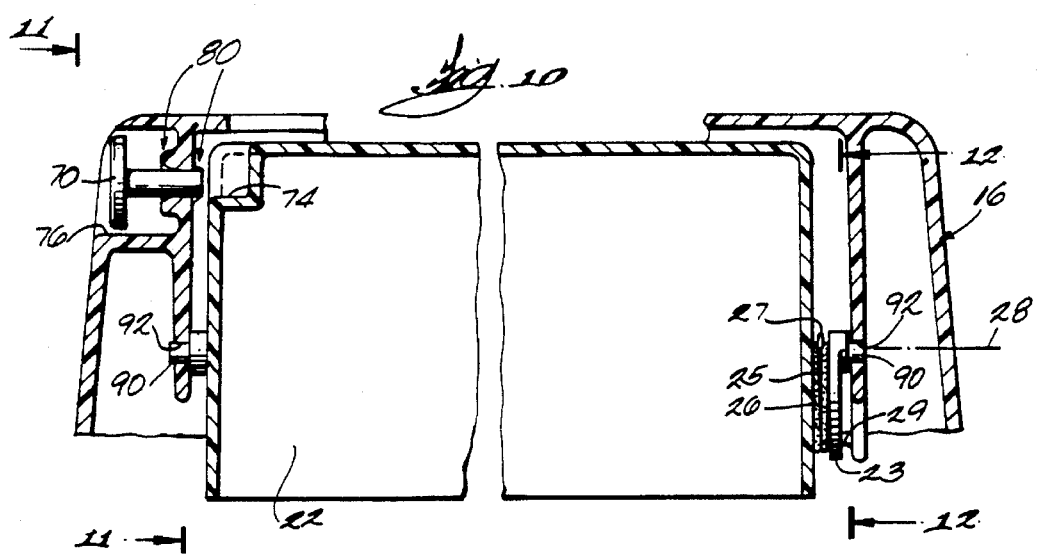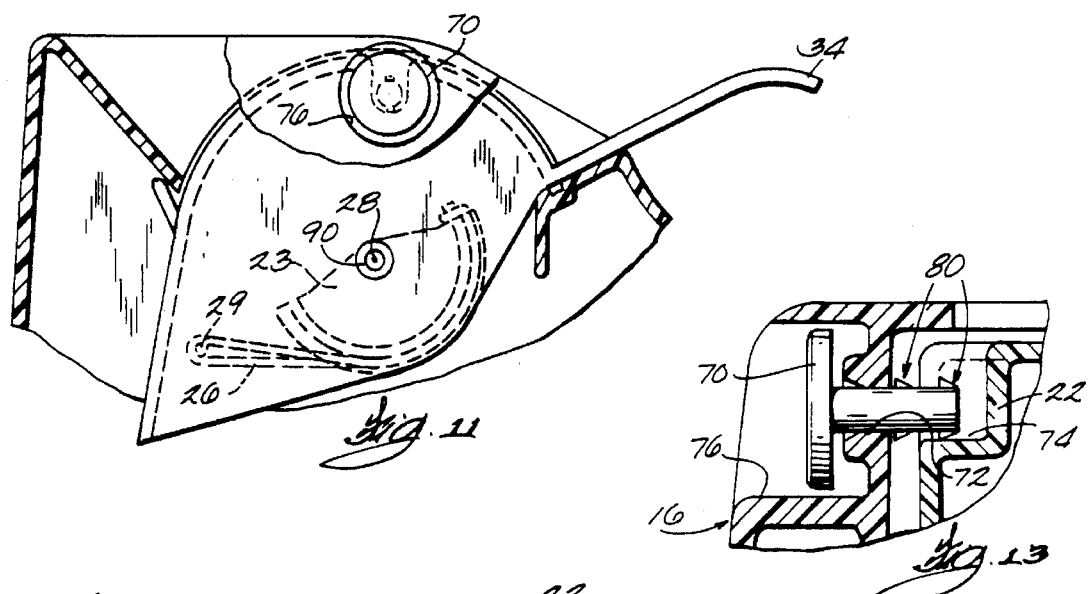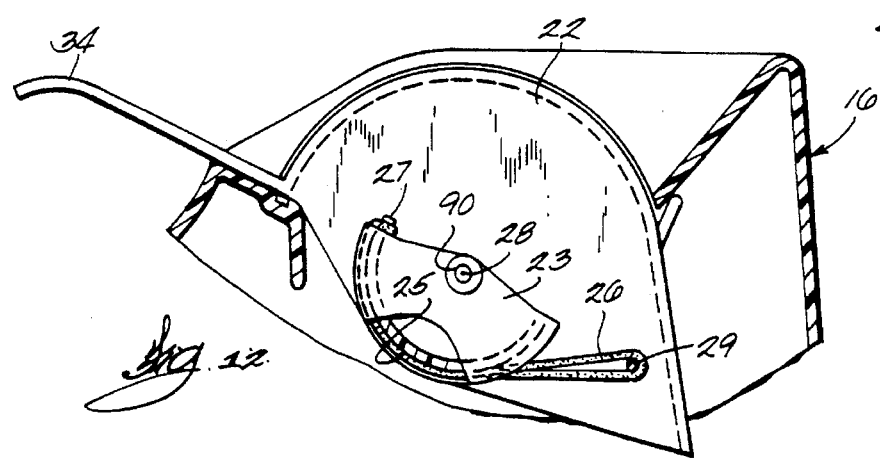

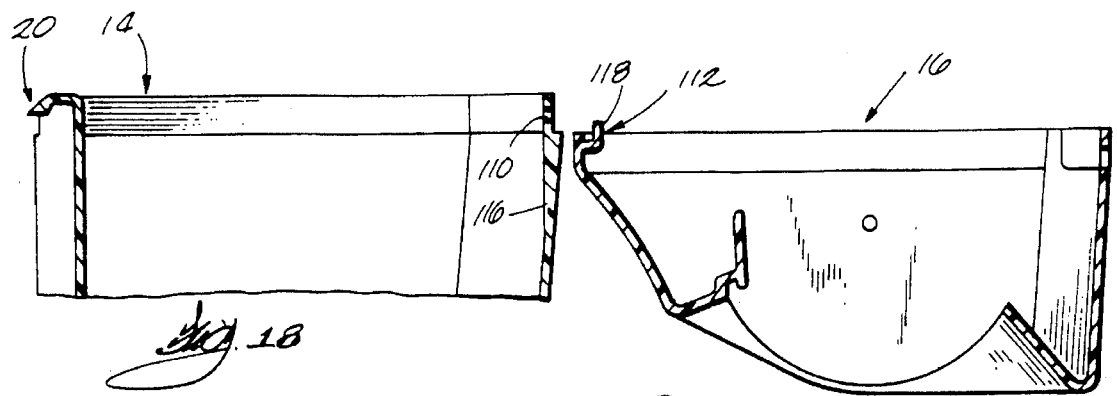
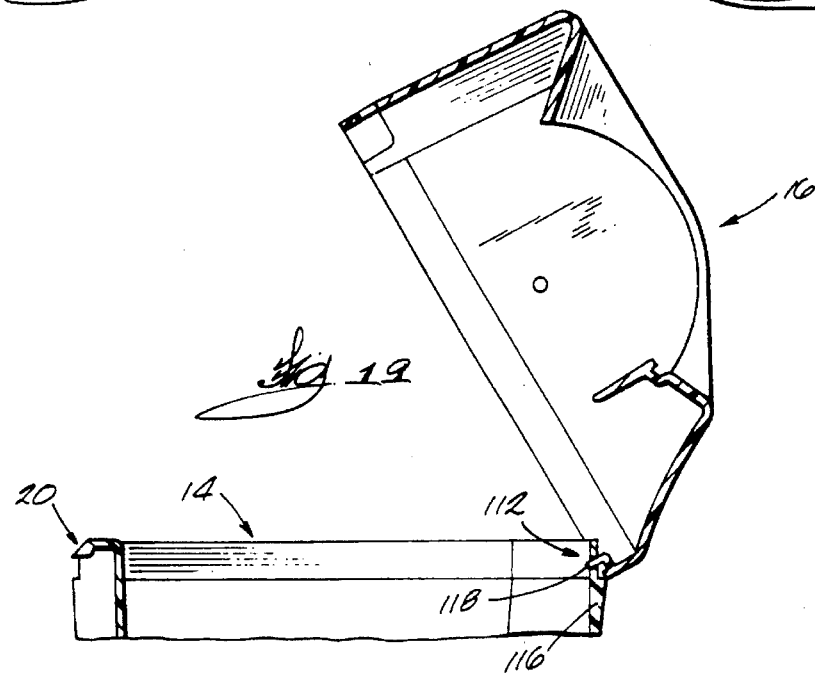
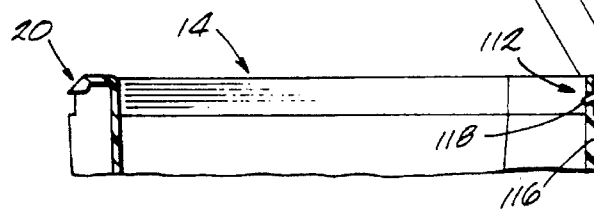
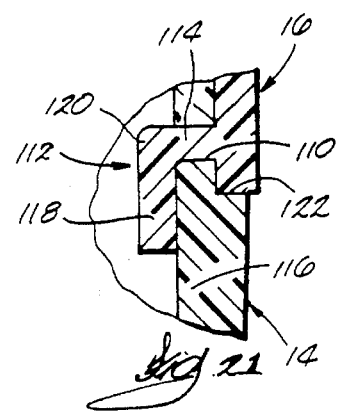
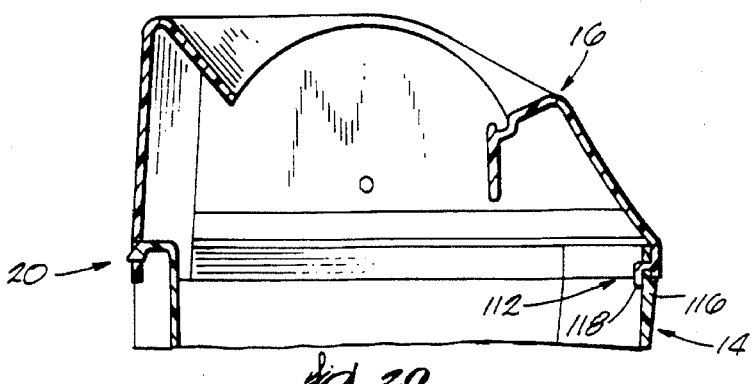

SHARPS DISPOSAL CONTAINER

RELATED APPLICATION

This is a divisional of application Ser. No. 08/045,830 filed Apr. 9, 1993, now U.S. Pat. No. 5,413,243, which is a continuation of Ser. No. 07/651,294 filed Feb. 5, 1991, now abandoned, which is a continuation of application Ser. No. 07/309,208 filed Dec. 20, 1988, now abandoned, which is a continuation-in-part of application Ser. No. 07/040,430, filed Apr. 30, 1987, issued as U.S. Pat. No. 4,736,860 on Apr. 12, 1988 and entitled "SHARPS DISPOSAL CONTAINER".

BACKGROUND OF THE INVENTION

The invention relates to sharps disposal apparatus, i.e., apparatus used in hospitals for containing sharp items such as used hypodermic needles.

Various government agencies recommend or require that hospitals provide a sharps disposal unit in each patient room. These units are intended to prevent used sharp items from causing injury to or infecting patients and hospital personnel and to prevent patients from stealing these items. Theft of used hypodermic needles (typically by intravenous drug users) is becoming a matter of great concern because of the rapid spread of AIDS. On the other hand, there is currently an emphasis in hospitals to make patient rooms more comfortable by improving their appearance and minimizing the amount of medical equipment therein.

Furthermore, government regulations require that some terminal treatment be applied to contaminated waste prior to disposal. In the case of sharps disposal units, this generally means incineration or steam sterilization.

SUMMARY OF THE INVENTION

The invention provides a sharps disposal unit that is easy to manufacture and assemble, is easily removed by authorized personnel but resists unauthorized tampering, is easy to use, has a pleasant appearance, and can be steam sterilized.

More particularly, the invention provides an apparatus comprising a container including a base and a cover connected to the base by an integral hinge. The cover is originally open so that the container can be nested with another container for shipping. The base and the cover include permanently interlocking means so that the container can be permanently closed after shipping.

The cover, which forms the upper portion of the container, includes a door which is manually movable between a closed position and an open position and which is biased toward the closed position. The container is completely closed when the door is in the closed position. Preferably, the door can be opened with one hand holding an object, e.g., a used hypodermic syringe, to be placed in the container.

Additionally, the apparatus comprises means for preventing removal of the contents of the container when the door is in the open position. Thus, the door can be opened to permit insertion of additional contents, but not to remove the present contents. Furthermore, the apparatus comprises means for selectively and permanently locking the door in the closed position when the container is full. In the preferred embodiment, this means includes a pin which is inserted through the container and into the door to prevent movement of the door relative to the container.

The apparatus further comprises a bracket that can be securely mounted on a wall by screws or other suitable means. The sides of the bracket extend generally vertically and slide into complementary slots formed on the back of the container. To attach the container to the bracket, the container is located above the bracket with the sides of the bracket aligned with the slots and is then lowered onto the bracket so that the sides of the bracket slide into the slots.

The bracket and container also include means for preventing unauthorized removal of the container from the bracket and for permitting authorized removal of the container from the bracket. Preferably, this preventing means includes, on the bracket, a resilient projection which is normally in a securing position and which is deflectible to a releasing position. The projection is in the securing position and extends into a recess in the container when the container is secured on the bracket. The preventing means also includes key means for deflecting the projection from the securing position to the releasing position. When the container is secured on the bracket, the projection prevents removal of the container from the bracket unless the key means is used to deflect the projection to the releasing position.

Preferably, the container, the bracket, and the door are all molded in one piece by conventional plastic injection methods. Each piece is molded with a simple two-piece mold that requires no cores or moving parts. The pieces snap together so that no tools are required for assembly. Also, the pieces are made of a plastic that is suitable for steam sterilization.

Other features and advantages of the invention will become apparent to those skilled in the art upon review of the following detailed description and claims.

DESCRIPTION OF THE DRAWINGS

FIG. 1 is a perspective view of an apparatus embodying the invention.

FIG. 2 is a vertical cross sectional view of the apparatus with the door and cover closed.

FIG. 3 is a partial view similar to FIG. 2 with the cover open and the door closed.

FIG. 4 is a partial view similar to FIG. 2 with the cover closed and the door open.

FIG. 5 is a cross-sectional view taken along line 5—5 in FIG. 2.

FIG. 6 is a front elevational view of the bracket.

FIG. 7 is a rear elevational view of the container.

FIG. 8 is a partial view similar to FIG. 2 showing the key releasing the container.

FIG. 9 is a perspective view of the key.

FIG. 10 is a view taken along line 10—10 in FIG. 2.

FIG. 11 is a view taken along line 11—11 in FIG. 10.

FIG. 12 is a view taken along line 12—12 in FIG. 10.

FIG. 13 is an enlarged view of the upper left-hand portion of FIG. 10 with the pin in the locking position.

FIG. 18 is a partial vertical, cross-sectional view of a second alternative embodiment of the invention with the cover disconnected from the base and without the door.

FIG. 19 is a view similar to FIG. 18 with the cover partially connected to the base.

FIG. 20 is a view similar to FIG. 18 with the cover fully connected to the base.

FIG. 21 is an enlarged view of a portion of FIG. 20.

Figure 14:
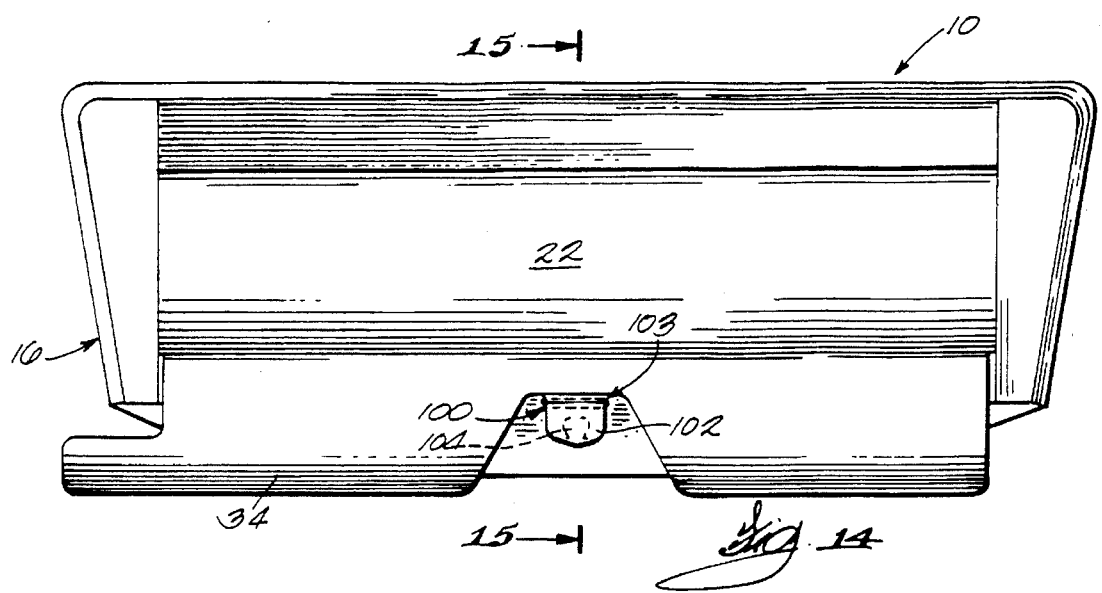
FIG. 14 is a top view of a container of an alternative embodiment of the invention.
Figure 15:
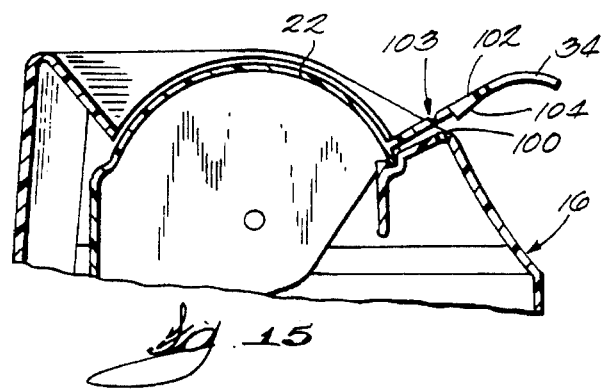
FIG. 15 is a view taken along line 15—15 in FIG. 14.

Before one embodiment of the invention is explained in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

An apparatus 10 embodying the invention is illustrated in the drawings. As shown in FIGS. 1 and 2, the apparatus 10 comprises a container 12 including a base 14, and a cover 16 connected to the base 14 by an integral hinge 18. The cover 16 is movable relative to the base 14 between an open position (FIG. 3) and a closed position (FIGS. 1, 2 and 4). In order to save space for shipping, the container 12 can be nested with other containers when the cover 16 is in the open position.

The container 12 further includes means for selectively and permanently securing the cover 16 in the closed position, so that the cover 16 cannot be opened once it is closed. While various suitable means can be employed, in the preferred embodiment, this means includes integral, non-reversible snap fasteners 20 on the base 14 and on the cover 16.

The container 12 further includes a door 22 which is located adjacent an opening 24 in the cover 16, which is manually movable between a closed position (FIGS. 1, 2, and 3) and an open position (FIG. 4), and which is biased toward the closed position. The container 12 is completely closed when the cover 16 is in its closed position and the door 22 is in its closed position. While various suitable means can be used for biasing the door 22 toward the closed position, in the illustrated construction, such means includes a rubber band 26 connected between the cover 16 and the door 22.

More particularly, the door 22 has thereon a semi-cylindrical portion 23 having as its axis of curvature the axis of rotation of the door 22. The portion 23 has therein a circumferentially extending recess 25 and has thereon, at one end of the recess 25, a projection 27. The cover 16 has thereon a projection 29, and the rubber band 26 is wound around the semi-cylindrical portion 23, in the recess 25, with one end of the rubber band 26 hooked on the projection 29 and with the opposite end of the rubber band 26 hooked on the projection 27. Thus, the rubber band 26 biases the door 22 in the clockwise direction as shown in FIG. 11.

As best shown in FIG. 2, the door 22 is partially cylindrical and is mounted in the cover 16, for rotation relative thereto about a generally horizontal axis 28, by oppositely extending projections 90 which extend along the axis 28 and which are received in bores 92 in the cover 16. The door 22 has thereon a fin 34 which limits pivotal movement of the door 22 beyond the closed position (counterclockwise in FIG. 2) and which facilitates manual movement of the door 22 from the closed position to the open position. Furthermore, the fin 34 allows the door 22 to be opened with one hand holding an object, e.g., a hypodermic needle, to be placed in the container 12.

The apparatus 10 further comprises means for preventing removal of the contents of the container 12 when the door 22 is in the open position. While various suitable means can be employed, in the preferred embodiment, this means includes an integral baffle 36 on the door 22. When the door 22 is moved to the open position, the baffle 36 moves into a position blocking the opening 24 in the cover 16, and the door 22 and baffle 36 form an upwardly opening "cradle" into which an object can be placed. The object is dumped out of the "cradle" and into the container 12 when the door 22 returns to the closed position.

In order to prevent the escape of the contents of the container 12 when the container 12 is full, the apparatus 10 further comprises means for selectively and permanently locking the door 22 in the closed position. While various suitable means can be used, in the illustrated construction, such means includes an aperture 72 in the cover 16 and an aperture or recess 74 in the door 22. The locking means also includes a pin 70 which extends through the aperture 72 and which is movable between a first or unlocked position wherein the pin 70 is removed from the recess 74 and a second or locked position wherein the pin 70 extends into the recess 74 when the door 22 is in the closed position.

The locking means also includes interengaging means on the pin 70 and on the cover 16 for securing the pin 70 in the second or locked position. Preferably, as shown in FIGS. 10 and 13, the pin 70 has thereon two axially spaced sets of projections 80 which permit movement of the pin 70 to the right as shown in the drawings or into the aperture 72 in the cover 16, but prevent movement of the pin 70 to the left or out of the aperture 72. When the pin 70 is in the unlocked position, as shown in FIG. 10, the pin 70 is only partially inserted into the aperture 72. In this position, the inner or right set of projections 80 engages the cover 16 to prevent outward movement of the pin 70, but the pin 70 does not extend into the recess 74 in the door 22. Thus, the door 22 is free to pivot about the axis 28. The pin 70 is moved to the locked position simply by pushing the head of the pin 70 inwardly when the door 22 is in the closed position. When the pin 70 is in the locked position, as shown in FIG. 13, the second or left set of projections 80 engages the cover 16 to prevent outward movement of the pin 70, the inner end of the pin 70 extends into the recess 74 to lock the door 22 in the closed position, and the head of the pin 70 fits snugly into a recess or counterbore 76 in the cover 16 so that the pin 70 is not removable once it is fully inserted.

The apparatus 10 further comprises a bracket 44 adapted to be securely mounted on a wall by screws or other suitable means. Preferably, screws 45 are inserted through apertures 46 in the bracket 44. The sides of the bracket 44 extend generally vertically and have thereon integral, forwardly offset tabs or projections 48. As shown in FIG. 6, the tabs 48 converge slightly toward their upper ends.

The apparatus 10 further comprises interengaging means on the bracket 44 and on the container 12 for securing the container 12 to the bracket 44. While various suitable means can be employed, in the preferred embodiment, such means includes, on the bracket 44, the tabs 48, and, on the container 12, a pair of integral slots 50 positioned so as to slidably receive the tabs 48. As shown in FIG. 7, the slots 50 converge in the same manner as the tabs 48, so that the lower ends of the slots 50 are slightly farther apart than are the upper ends of the tabs 48. The container 12 is mounted on the bracket 44 by holding the container 12 above the bracket 44, aligning the slots 50 with the tabs 48, and lowering the container 12 onto the bracket 44 so that the tabs 48 slide into the slots 50. Because the lower ends of the slots 50 are farther apart than the upper ends of the tabs 48, it is easy to align the tabs 48 and the slots 50. Downward movement of the container 12 relative to the bracket 44 is limited by a lip 52 on the lower end of the bracket 44.

The apparatus 10 further comprises means for preventing unauthorized removal of the container 12 from the bracket 44 and for permitting authorized removal of the container 12 from the bracket 44. While various suitable means can be used, in the illustrated construction, this means includes a recess 54 in the rear wall of the container 12, and a pair of resilient, downwardly extending projections 56 on the bracket 44. The projections 56 are normally in a securing position (FIG. 2) and are deflectible to a releasing position (FIG. 8). The projections 56 are in the securing position and extend into the recess 54 when the container 12 is secured on the bracket 44, so that the projections 56 prevent upward movement of the container 12. The means for preventing unauthorized removal of the container 12 also includes key means for deflecting the projections 56 from the securing position to the releasing position. In the preferred embodiment, the key means includes a key 58 (FIGS. 8 and 9) having a pair of generally parallel, spaced apart prongs 60 which are insertable through apertures in the base 14 and into engagement with the projections 56 for moving the projections 56 from the securing position to the releasing position. When the projections 56 are in the releasing position, the container 12 can be moved upwardly relative to the bracket 44 and thus removed from the bracket 44.

An alternative embodiment of the invention is illustrated in FIGS. 14–17. Except as explained hereinafter, the alternative embodiment is substantially identical to the preferred embodiment, and common elements have been given the same reference numerals.

Figure 17:
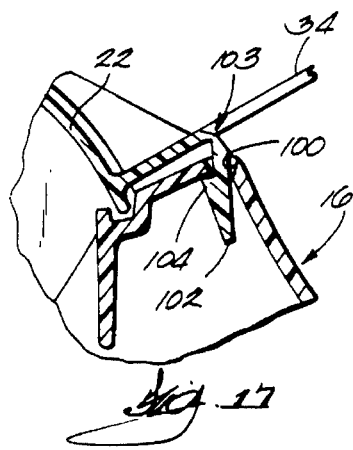
FIG. 17 is an enlarged view of a portion of FIG. 16.
Figure 16:
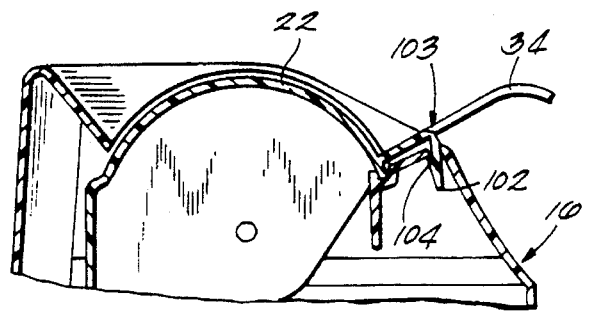
FIG. 16 is a view similar to FIG. 15 with the door locked in the closed position.

In the alternative embodiment, the apparatus 10 comprises alternative means for selectively and permanently locking the door 22 in the closed position, i.e., an alternative to the pin 70 of the preferred embodiment. More particularly, the means for selectively and permanently locking the door 22 in the closed position includes a slot 100 in the cover 16, and a projection or tab 102 which is pivotally mounted on the door 22 by a living hinge 103 and which is pivotally movable between a first or unlocked position (FIGS. 14 and 15) wherein the projection 102 does not extend into the slot 100 but extends generally coplanar with the fin 34, and a second or locked position (FIGS. 16 and 17) wherein the projection 102 extends into the slot 100 when the door 22 is in the closed position. The locking means also includes interengaging means on the projection 102 and on the cover 16 for securing the projection 102 in the slot 100. While various suitable securing means can be employed, in the illustrated construction, the securing means includes a triangular, wedge-shaped tooth or protuberance 104 which extends from the underside of the projection 102, which facilitates insertion of the projection 102 into the slot 100, and which, as shown in FIGS. 16 and 17, engages the inside of the cover 16 when the projection 102 is fully inserted into the slot 100 so that the projection 102 is not removable from the slot 100.

A second alternative embodiment of the invention is illustrated in FIGS. 18–21. Except as explained hereinafter, the second alternative embodiment is substantially identical to the preferred embodiment, and common elements have been given the same reference numerals.

In the second alternative embodiment, the container 12 includes a base 14 and a separate cover 16. The container 12 also includes selectively interengageable hinge means for pivotally connecting the cover 16 to the base 14. While various suitable hinge means can be employed, in the second alternative embodiment, the hinge means includes a plurality of spaced slots 110 located in the base 14 adjacent the upper, front edge of the base 14, and a corresponding number of integral, spaced L-shaped projections or teeth 112 located on the cover 16 adjacent the lower, front edge of the cover 16. Each of the teeth 112 includes (see FIG. 21) a first portion 114 extending inwardly and generally perpendicular to the front wall 116 of the cover 16, and a second portion 118 extending generally perpendicular to the first portion 114 and downwardly when the cover 16 is fully connected to the base 14. The first and second portions 114 and 118 are connected by an integral arcuate portion 120 having concentric inner and outer radii.

The cover 16 is connected to the base 14 by inserting the second portions 118 of the teeth 112 into their respective slots 110, as shown in FIG. 19. The cover 16 is then rotated (counter-clockwise as shown in FIG. 19) relative to the base 14 until the first portions 114 of the teeth 112 are received in their respective slots 110 and the snap fasteners 20 secure the cover 16 in the closed position relative to the base 14, as shown in FIG. 20. The inner and outer radii of the arcuate portions 120 of the teeth 112 facilitate insertion of the teeth 112 into the slots 110 and rotation of the cover 16 relative to the base 14. When the cover 16 is in the closed position relative to the base 14, the second portions 118 of the teeth 112 bear tightly against the inner face of the front wall of the base 14. As shown in FIG. 21, the outer face of the base 14 has thereon a ridge or rabbet 122 that mates with the bottom edge of the front wall 116 of the cover 16 so that any needle that might penetrate the extremely small clearance between one of the teeth 112 and its respective slot 110 cannot extend through to the exterior of the container 12.

The use of a cover 16 that is separate from the base 14 provides at least two advantages. First, this permits the container 12 to be economically manufactured by multicavity molding. Second, this permits a standard cover 16 to be used on containers 12 of varying sizes. With a separate cover 16, the size of a container 12 can be varied simply by varying the depth of the base 14.

Various features of the invention are set forth in the following claims.

We claim:

1. A sharps container apparatus comprising a container including a door manually movable between a closed position and an open position, said container being completely closed when said door is in said closed position, and a mechanism for selectively and permanently locking said door in said closed position, said locking mechanism including a recess in one of said container and said door, and a projection which is pivotally connected to the other of said container and said door by a living hinge for movement relative to said other of said container and said door between a first position wherein said projection cannot be inserted into said recess regardless of the position of said door and a second position wherein said projection extends into said recess when said door is in said closed position.

2. Apparatus as set forth in claim 1 wherein said recess is a slot in said container.

3. Apparatus as set forth in claim 1 wherein said locking mechanism includes interengaging means on said projection and on said one of said container and said door for securing said projection in said second position.

4. Apparatus as set forth in claim 3 wherein said interengaging means includes a wedge-shaped tooth located on said projection.

5. Apparatus as set forth in claim 1 wherein said projection is mounted on said door for pivotal movement between said first and second positions, and wherein said projection moves with said door as said door moves between said open and closed positions.

6. Apparatus as set forth in claim 1 wherein said projection can be inserted into said recess only after moving said projection relative to said other of said container and door without moving said door relative to said container.

7. A sharps container apparatus comprising a container including a door manually movable between a closed position and an open position, said container being completely closed when said door is in said closed position, and a mechanism for selectively and permanently locking said door in said closed position, said locking mechanism including a recess in one of said container and said door, and a projection which is pivotally connected to the other of said container and said door by a living hinge for movement relative to said other of said container and said door between a first position wherein said projection is removed from said recess so that said door is unlocked when said door is in said closed position and a second position wherein said projection extends into said recess so that said door is locked when said door is in said closed position, such that a user can either lock said door in said closed position or leave said door unlocked when said door is in said closed position.

8. Apparatus as set forth in claim 7 wherein said recess is a slot in said container.

9. Apparatus as set forth in claim 7 wherein said locking mechanism includes interengaging means on said projection and on said one of said container and said door for securing said projection in said second position.

10. Apparatus as set forth in claim 9 wherein said interengaging means includes a wedge-shaped tooth located on said projection.

11. Apparatus as set forth in claim 7 wherein said projection is mounted on said door for pivotal movement between said first and second positions, and wherein said projection moves with said door as said door moves between said open and closed positions.

12. Apparatus as set forth in claim 7 wherein said projection can be inserted into said recess only after moving said projection relative to said other of said container and door without moving said door relative to said container.

13. Apparatus as set forth in claim 7 wherein said door cannot be moved beyond said closed position in the direction away from said open position.

14. A sharps container apparatus comprising a container including a door manually movable between a closed position and an open position, said container being completely closed when said door is in said closed position, and a mechanism for selectively and permanently locking said door in said closed position, said locking mechanism including a recess in said container, and a projection which is permanently located on said door, which moves with said door as said door moves between said open and closed positions and which is movable relative to said door between a first position wherein said projection cannot be inserted into said recess regardless of the position of said door and a second position wherein said projection extends into said recess when said door is in said closed position.

15. Apparatus as set forth in claim 14 wherein said recess is a slot in said container.

16. Apparatus as set forth in claim 14 wherein said locking mechanism includes interengaging means on said projection and on said container for securing said projection in said second position.

17. Apparatus as set forth in claim 16 wherein said interengaging means includes a wedge-shaped tooth located on said projection.

18. Apparatus as set forth in claim 14 wherein said projection can be inserted into said recess only after moving said projection relative to said door without moving said door relative to said container.

19. A sharps container apparatus comprising a container including a door manually movable between a closed position and an open position, said container being completely closed when said door is in said closed position, and a mechanism for selectively and permanently locking said door in said closed position, said locking mechanism including a recess in said container, and a projection which is permanently located on said door, which moves with said door as said door moves between said open and closed positions and which is movable relative to said door between a first position wherein said projection is removed from said recess so that said door is unlocked when said door is in said closed position and a second position wherein said projection extends into said recess so that said door is locked when said door is in said closed position, such that a user can either lock said door in said closed position or leave said door unlocked when said door is in said closed position.

20. Apparatus as set forth in claim 19 wherein said recess is a slot in said container.

21. Apparatus as set forth in claim 19 wherein said locking mechanism includes interengaging means on said projection and on said container for securing said projection in said second position.

22. Apparatus as set forth in claim 21 wherein said interengaging means includes a wedge-shaped tooth located on said projection.

23. Apparatus as set forth in claim 19 wherein said projection can be inserted into said recess only after moving said projection relative to said door without moving said door relative to said container.

24. Apparatus as set forth in claim 19 wherein said door cannot be moved beyond said closed position in the direction away from said open position.

* * * * *